US00PP28932P2

(12) United States Plant Patent
Walla et al.

(10) Patent No.: US PP28,932 P2
(45) Date of Patent: Feb. 6, 2018

(54) ***MORUS* PLANT NAMED 'TRADER'**

(50) Latin Name: *Morus alba*
Varietal Denomination: Trader

(71) Applicants: James Walla, Fargo, ND (US); Michael Edward Kjelland, Valley City, ND (US)

(72) Inventors: James Walla, Fargo, ND (US); Michael Edward Kjelland, Valley City, ND (US)

( * ) Notice: Subject to any disclaimer, the term of this patent is extended or adjusted under 35 U.S.C. 154(b) by 0 days.

(21) Appl. No.: 15/330,025

(22) Filed: Jul. 27, 2016

(51) Int. Cl.
*A01H 5/08* (2006.01)

(52) U.S. Cl.
USPC ..... Plt./156

(58) Field of Classification Search
USPC ..... Plt./156
See application file for complete search history.

*Primary Examiner* — Annette H Para
(74) *Attorney, Agent, or Firm* — Penny J. Aguirre

(57) ABSTRACT

A new cultivar of *Morus* plant named 'Trader' that is characterized by its very good cold hardiness and little or no branch die back when grown in North Dakota, its dark purple-black fruit annually with berries ripening sequentially from mid July to mid September in North Dakota, its fruit that lack viable seed with very little seed produced, its plant height of 35 feet (125 year-old tree), its plant habit with a spherical crown that is relatively open (30% porosity when leaved out), and its resistance to spotted-wing drosophila.

2 Drawing Sheets

Botanical classification: *Morus alba.*
Cultivar designation: 'Trader'.

BACKGROUND OF THE INVENTION

The present invention relates to a new and distinct cultivar of mulberry plant, botanically known as *Morus alba* 'Trader' and will be referred to hereinafter by its cultivar name, 'Trader'. 'Trader' is grown for production of fruit by home gardeners and is suitable for growing in northern climates.

'Trader' was discovered by one of the Inventors in 2000 as the sole survivor from a grove of unnamed seedlings of *Morus alba* planted by a German immigrant in about 1890 near Oriska, Barnes county, N.Dak. (from reports of family members). There are no other mulberry trees in the area known to the Inventors.

Asexual propagation of the new cultivar was first accomplished by one of the Inventors by softwood stem cuttings in Oriska, Barnes County, N.Dak. in 2002. Asexual propagation of the new cultivar by softwood stem cuttings has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Trader' as a new and unique cultivar of *Morus.*

1. 'Trader' exhibits very good cold hardiness and little or no branch die back when grown in North Dakota.
2. 'Trader' exhibits dark purple-black fruit annually with berries ripening sequentially from mid July to mid September in North Dakota.
3. 'Trader' exhibits fruit that lack viable seed with very little seed produced.

4. 'Trader' exhibits a height of 35 feet (125 year-old tree).
5. 'Trader' exhibits a plant habit with a spherical crown that is relatively open (30% porosity when leaved out).
6. 'Trader' exhibits resistance to spotted-wing drosophila.

'Trader' can be most closely compared to *Morus* cultivars 'Illinois Everbearing' (not patented) (*Morus alba*×*Morus rubra*) and 'Northrup' (not patented) (*Morus rubra*). 'Illinois Everbearing' is similar to 'Trader' in being reported to have good cold hardiness and in producing nearly seedless fruit that is produced sequentially throughout the season. 'Illinois Everbearing' differs most significantly from 'Trader' in having less cold hardiness with a high level of branch dieback occurring when grown in North Dakota under similar conditions as 'Trader', in lacking fruit production when grown in North Dakota, in having leaves that have more deeply serrated margins with sharp tips, lobed even when mature, and a rough surface, and in exhibiting stipules. 'Northrup' is similar to 'Trader' in being reported to have good cold hardiness and in being self-fertile. 'Northrup' differs from 'Trader' in having fruit that ripens uniformly at one time instead of sequentially, in reaching a much taller height, and in showing less cold hardiness with branch die-back occurring in cold winters.

BRIEF DESCRIPTION OF THE DRAWINGS

The accompanying colored photographs illustrate the overall appearance and distinct characteristics of the new *Morus*. The photographs were taken of an eight year-old tree as grown in the ground in Valley City, N.Dak.

The photograph in FIG. 1 provides a view of the plant habit of 'Trader'.

Figure 1:
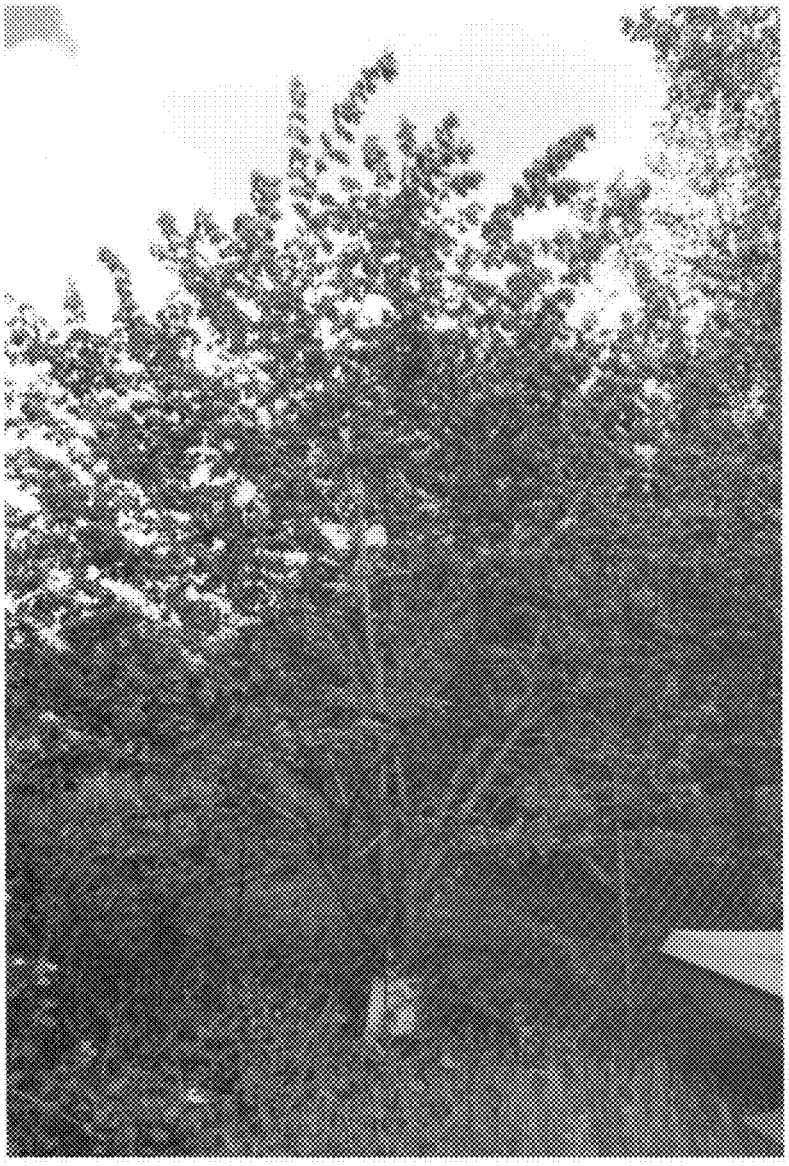
Figure 2:
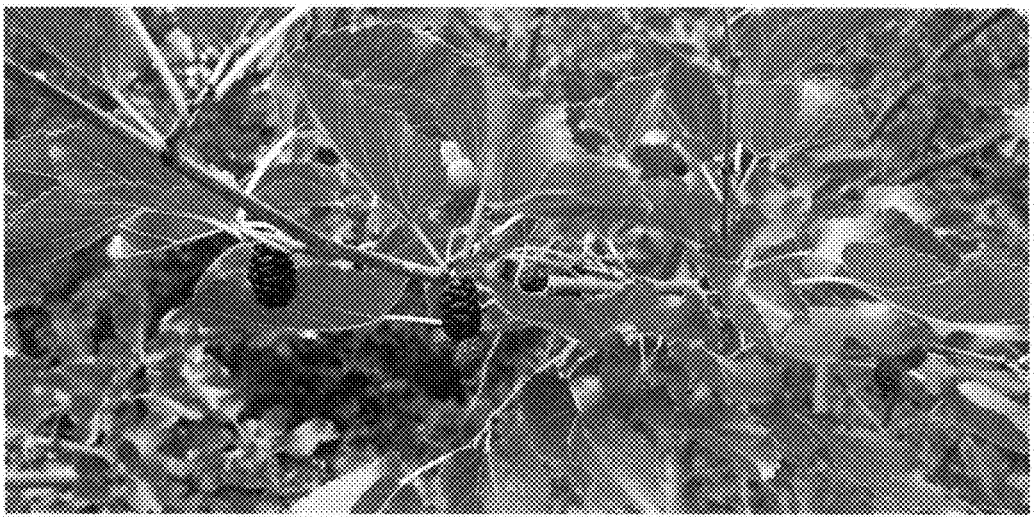

The photograph in FIG. 2 provides a close-up view of the foliage and sequential fruit ripening of 'Trader'.

Figure 3:
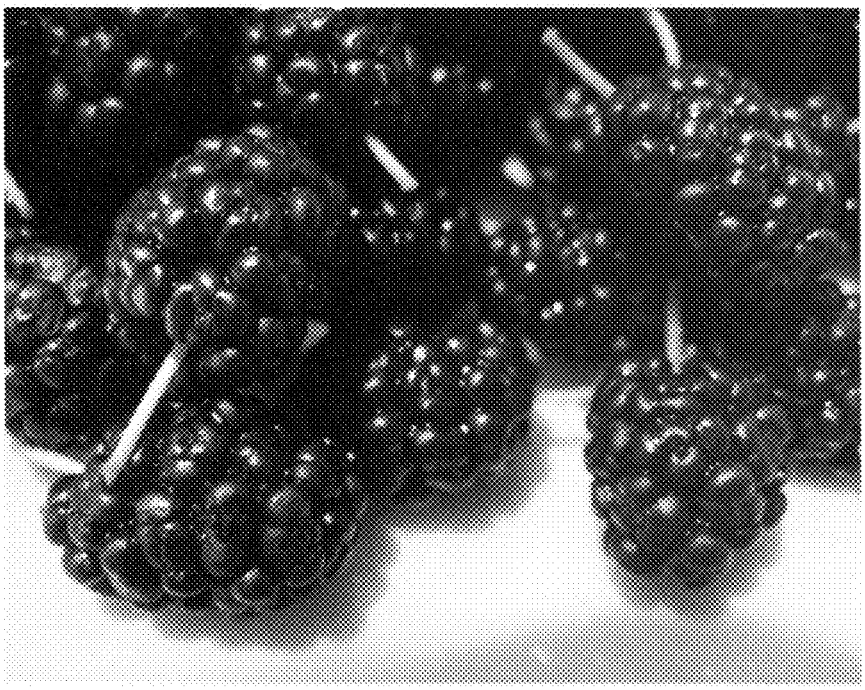

The photograph in FIG. 3 provides a close-up view of the mature fruit of 'Trader'.

The colors in the photographs are as close as possible with the photographic and printing technology utilized. The colors in the photograph may differ slightly from the color values cited in the detailed botanical description, which accurately describe the colors of the new *Morus*.

DETAILED BOTANICAL DESCRIPTION OF THE PLANT

The following is a detailed description of four year-old plants of the new cultivar as grown outdoors in a 3-gallon container in Fargo, N.Dak. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Early summer in North Dakota.

*Plant type*.—Fruit producing deciduous tree.

*Plant habit*.—Spherical crown that is relatively open (30% porosity when leaved out).

*Height and spread*.—Reaches an average of 6 m (19.5 ft) in height and 4 m (13 ft) in spread as a 13 year-old tree and the original tree (125 years old) is about 11 m in height and 9.1 meters in spread.

*Cold hardiness*.—Extremely cold hardy in comparison to other cultivars that are considered cold-hardy, hardy at least to U.S.D.A Zone 4a by the 2012 map (3b on the 1990 map), the original tree survived −44° F. in 1994 (Zone 2b).

*Diseases and pests*.—Has shown resistance to spotted-wing drosophila (*Drosophila suzukii*).

*Root description*.—Fibrous and fine, 162D in color.

*Branching habit*.—Well-branched with open lateral branches.

*Propagation*.—Softwood stem cuttings.

*Root development*.—Roots initiate in 15 to 25 days, after several transplants, a tree 60 cm to 1.2 m in height is produced in about one year from a rooted cutting.

*Growth rate*.—Very vigorous as a young plant.

Branch description:

*Twigs*.—An average of 19 cm in length and 2.5 mm in width, color between 147D and 195A with slight anthocyanin of N166A (on upper surface more prominently), surface glabrous, buds at leaf nodes; an average of 3 mm in length and 2 mm in width, triangular in shape, surface imbricate, 166A and 164B in color with scale margins 200B with a thin line of 155A, acute apex with some bud scales pulled away, lenticels; oblong to oval in shape, an average of 2 mm in length and 1 mm in width, about 7 per stem 2 cm in length, 199C in color.

*Mature branches* (*more than one year in age*).—An average of 32 cm in length and 4 mm in width (at mid point), a blend of 167A and 195A, surface relatively smooth, lenticels; about 15 per stem 3.5 cm in length, an average of 1.5 mm in length and 0.5 mm in width, horizontal, and 165D in color.

*Main stem*.—1.2 m in length, 1.5 cm in width 10 cm from soil line, surface is rough barked near base and fine fissured toward apex, color a blend of 167A and 165A, lenticels; about 20 per stem 3.5 cm in length, an average of 1.5 mm in length and 0.5 mm in width, horizontal, and 165D in color.

*Stipules*.—Not observed.

*Internode length*.—Branches; average of 7 cm, twigs; a average of 3 cm.

Foliage description:

*Leaf shape*.—Ovate to cordate.

*Leaf division*.—Simple.

*Leaf attachment*.—Petiolate.

*Leaf aspect*.—Held slightly curved inward and straight outward from petiole.

*Leaf size*.—Up to 13 cm in length and 9 cm in width.

*Leaf quantity*.—An average of 6 per branch 18 cm in length.

*Internode length*.—An average of 3.5 cm.

*Leaf base*.—Cordate.

*Leaf apex*.—Acute.

*Leaflet venation*.—Pinnate, conspicuous on lower surface only, color on upper surface; N144D, color on lower surface; 145C.

*Leaf margins*.—Un-lobed to tri-lobed (when Juvenile), all margins serrated with rounded tips.

*Leaf arrangement*.—Alternate, monopodial growth at tip zig-zag.

*Leaf surface*.—Upper surface glabrous and satiny, lower surface glabrous and dull.

*Leaf color*.—New growth; upper and lower surface 144A, mature growth; upper surface a color between 137B and 144A, lower surface 138B.

*Leaf substance*.—Thin.

*Petioles*.—Round in shape, an average of 3 cm in length and 2.5 mm in width, color; 160B, surface very sparsely pubescent on upper surface (more so near leaf) and glabrous on lower surface, held at an average angle of 45° to stem and slightly curved downward, moderate in strength.

Inflorescence description:

*Inflorescence type*.—Dense spikes of female only flowers (dioecious).

*Lastingness of inflorescence*.—About 4 days for stigma in plume, stigma is persistent as it forms fruit.

*Inflorescence*.—An average of 8 mm in length and width.

*Rachis* (*peduncle*).—Oval in shape, an average of 1 cm in length and up to 0.7 mm in width, no internodes between flowers, flowers are present on upper 5 mm in rachis, 144B in color, sparsely pubescent surface, strong, held at an average angle of 45°.

*Pedicels*.—None, sessile to rachis.

*Flower buds*.—Triangular in shape with a wide flat bottom and apex narrowing to a point, up to 2 mm in width and length, 144A in color, surface is glabrous.

*Flower type*.—Comprised only of a stigma, ovary, and calyx surrounding the ovary.

*Flower number*.—An average of 25 per spike.

*Flower size*.—Average of 3.5 mm in depth and diameter.

*Sepals*.—3, obovate in shape, held surround ovary, an average of 2 mm in width and 3 mm in length, truncate base, rounded apex, margins entire, color upper and lower surface; 144D, glabrous and satiny surface.

*Petals*.—None, apetalous.

*Androecium*.—Not present.

*Gynoecium.*—1 pistil, styles; 2-branched, an average of 2 mm in length and N200A in color when mature, stigmatic plume on surface of style 155A in color, ovary; about 2 mm in length and 1.5 mm in width, ovate in shape, and 155D in color.

Fruit description:

*Fruit number.*—An average of 10 per twig.

*Fruit size.*—Aggregate an average of 1.1 cm in width and 1.65 cm in length.

*Fruit shape.*—Oblong.

*Druplets.*—An average of 40 per aggregate fruit, roughly ovate in shape, an average of 2.5 mm in diameter and height, color when beginning to ripen; 35B, color when maturing; a blend of 184A, 182A, 187A, and N186A, color when mature (skin and flesh); N186A with very base 181A, surface is glossy, style and stigma; persistent at maturity and extends from druplet an average of 1 mm when immature and lays on surface when mature, very fine, 200A in color.

*Persistence of sepals.*—Persistent, form skin of the fruit.

*Receptacle.*—Oblong in shape, an average of 2 mm in diameter and 7 mm in length, N186A in color.

*Fruit stalk.*—An average of 5 mm in length and 1 mm in width, very sparsely pubescent surface, 199B in color.

*Fruit maturity.*—Ripening sequentially from mid July to mid September in North Dakota.

*Seed.*—Oval in shape, 1 per druplet if present, 2.5 mm in length, 1 mm in width, 176A in color and lacks viability.

*Flavor.*—Mulberry, sweet and slightly tart.

*Fruit weight.*—An average of 0.5 grams per aggregate.

*Fruit firmness.*—Very firm.

It is claimed:

1. A new and distinct cultivar of *Morus* plant named 'Trader' as herein illustrated and described.

* * * * *